US011250955B2

(12) United States Patent
Chakraborty et al.

(10) Patent No.: US 11,250,955 B2
(45) Date of Patent: Feb. 15, 2022

(54) SYSTEMS AND METHODS FOR HEALTH EVALUATION AND MONITORING

(71) Applicant: VISA INTERNATIONAL SERVICE ASSOCIATION, San Francisco, CA (US)

(72) Inventors: Sukalyan Chakraborty, Palo Alto, CA (US); Nikhil Ghate, Palo Alto, CA (US); Santanu Deb Roy, Foster City, CA (US); Urjit Anand Khadilkar, Palo Alto, CA (US); Chanchal Ghosh, Palo Alto, CA (US)

(73) Assignee: VISA INTERNATIONAL SERVICE ASSOCIATION, San Francisco, CA (US)

( * ) Notice: Subject to any disclaimer, the term of this patent is extended or adjusted under 35 U.S.C. 154(b) by 309 days.

(21) Appl. No.: 16/526,599

(22) Filed: Jul. 30, 2019

(65) Prior Publication Data
US 2021/0035691 A1 Feb. 4, 2021

(51) Int. Cl.
*G16H 50/30* (2018.01)
*G06Q 30/06* (2012.01)

(52) U.S. Cl.
CPC ......... *G16H 50/30* (2018.01); *G06Q 30/0625* (2013.01)

(58) Field of Classification Search
CPC ......................... G16H 50/30; G06Q 30/0625
See application file for complete search history.

(56) References Cited

U.S. PATENT DOCUMENTS

| | | | | |
|---|---|---|---|---|
| 2014/0180784 A1* | 6/2014 | Martin | ............... | G06Q 30/0215 705/14.17 |
| 2015/0269346 A1* | 9/2015 | Lee | .................... | G06Q 30/0255 705/14.53 |
| 2019/0065692 A1* | 2/2019 | Connelly | ............... | G16H 40/20 |
| 2019/0180873 A1* | 6/2019 | Kartoun | ................ | G16H 50/70 |

* cited by examiner

*Primary Examiner* — Philip J Chea
*Assistant Examiner* — Hassan A Khan
(74) *Attorney, Agent, or Firm* — Loeb & Loeb LLP (57) ABSTRACT

A computer implemented method of determining a user health rating. The method may include evaluating transaction records in a user transaction history, determining whether the transactions are associated with positive or negative health, and generating a user health rating at least partially based on the transaction records.

20 Claims, 5 Drawing Sheets

SYSTEMS AND METHODS FOR HEALTH EVALUATION AND MONITORING

FIELD

The disclosure relates to systems and methods for evaluating and monitoring user health.

BACKGROUND

People are increasingly interested in monitoring personal health in various ways in order to learn to make better health decisions. Decisions to improve health may be related to exercise, diet, medical needs, etc. Additional data on personal habits may help educate people to make better health decisions.

SUMMARY

The following presents a simplified summary of the present disclosure in order to provide a basic understanding of some aspects of the disclosure. This summary is not an extensive overview of the disclosure. It is not intended to identify key or critical elements of the disclosure or to delineate the scope of the disclosure. The following summary merely presents some concepts of the disclosure in a simplified form as a prelude to the more detailed description provided below.

In some embodiments, the disclosure describes a computer implemented method of determining a user health rating. The method may include evaluating transaction records in a user transaction history, determining whether the transactions are associated with positive or negative health, and generating a user health rating that may be at least partially based on the transaction records.

BRIEF DESCRIPTION OF THE DRAWINGS

The disclosure may be better understood by references to the detailed description when considered in connection with the accompanying drawings. The components in the figures are not necessarily to scale, emphasis instead being placed upon illustrating the principles of the disclosure. In the figures, like reference numerals designate corresponding parts throughout the different views.

Persons of ordinary skill in the art will appreciate that elements in the figures are illustrated for simplicity and clarity so not all connections and options have been shown to avoid obscuring the inventive aspects. For example, common but well-understood elements that are useful or necessary in a commercially feasible embodiment are not often depicted in order to facilitate a less obstructed view of these various embodiments of the present disclosure. It will be further appreciated that certain actions and/or steps may be described or depicted in a particular order of occurrence while those skilled in the art will understand that such specificity with respect to sequence is not actually required. It will also be understood that the terms and expressions used herein are to be defined with respect to their corresponding respective areas of inquiry and study except where specific meaning have otherwise been set forth herein.

DETAILED DESCRIPTION

The present disclosure now will be described more fully hereinafter with reference to the accompanying drawings, which form a part hereof, and which show, by way of illustration, specific exemplary embodiments by which the disclosure may be practiced. These illustrations and exemplary embodiments are presented with the understanding that the present disclosure is an exemplification of the principles of one or more disclosures and is not intended to be limited to any one of the embodiments illustrated. The disclosure may be embodied in many different forms and should not be construed as limited to the embodiments set forth herein; rather, these embodiments are provided so that this disclosure will be thorough and complete, and will fully convey the scope of the disclosure to those skilled in the art. Among other things, the present disclosure may be embodied as methods or devices. Accordingly, the present disclosure may take the form of an entirely hardware embodiment, an entirely software embodiment or an embodiment combining software and hardware aspects. The following detailed description is, therefore, not to be taken in a limiting sense.

People's purchasing behavior and spending patterns may provide insight into their general health or other behavioral patterns and circumstances. For example, the types or categories of merchants people tend to transact with may translate into a health model that may be tracked over time. Accordingly, in some embodiments, the disclosure describes systems and methods for evaluating and monitoring user health based on various data sources, such as user purchase information. In some embodiments, a health monitoring system that may analyze user payment transaction data to generate a user health rating that is reviewable by the user via a user computing device. For example, the system may include evaluating each user transaction based on the type of merchant, timing of the transaction, frequency of transactions with that merchant or type of merchant, and other parameters to determine whether those transactions are reflective of positive or negative health outcomes. The user health rating may be tracked over time, and the user may be provided with updates and graphical reports depicting trends indicative of increasing or decreasing healthy behavior.

In some embodiments, the health monitoring system may include a generating a user health rating based on the user's spending patterns, buying age category, or other user-specific inputs. The health rating and other related information may be provided to the user via a user health application on a user computing device, for example. The user health application may provide graphical data indicating the user's health rating over time, the quantity of user purchases in varying merchant categories, etc., and may provide feedback on how the user may change purchasing patterns to achieve an improved health rating. In some embodiments, the user health application may provide a historical time line of the user health rating and may predict future ratings based on current purchasing habits. Additionally, in some embodiments, the user health application may provide a graphical user interface (GUI) indicating the factors in the user's purchasing or other habits that may be contributing to the user health rating, and how those may be changed.

In some embodiments, the disclosure describes a computer-implemented method comprising identifying a plurality of merchant category codes, assigning a merchant health rating to each of the plurality of merchant category codes, and receiving a user identifier of a user associated with a user account from a user computing device. Based on the user identifier, the method may include extracting an account transaction history for the user account. The account transaction history may include one or more user transaction records each associated with a merchant. The method may include identifying a merchant category code of the plurality of merchant category codes for the merchant associated with each of the one or more user transaction records and determining a transaction health rating for each of the one or more user transaction records based at least partially on the merchant health rating for the identified merchant category code for each of the one or more user transaction records. Based at least partially on the transaction health rating of the one or more user transaction records, the method may include determining a user health rating associated with the user account. The method may also include transmitting the user health rating to the user computing device.

In some embodiments, the disclosure describes a computer-implemented method comprising receiving a user identifier of a user associated with a user account from a user computing device. Based on the user identifier, the method may include extracting an account transaction history for the user account. The account transaction history may include a plurality of user transaction records each associated with a merchant, where the plurality of user transaction records may include a first user transaction record associated with a first merchant and a second user transaction record associated with a second merchant. The method may include identifying a first merchant category code for the first merchant and a second merchant category code for the second merchant, wherein the first merchant category code may be associated with a first merchant health rating and the second merchant category code may be associated with a second merchant health rating. The method may include determining a first transaction health rating for the first user transaction record based at least partially on the first merchant health rating and a second transaction health rating for the second user transaction record based at least partially on the second merchant health rating. Based at least partially on the first transaction health rating and the second transaction health rating, the method may include determining a user health rating associated with the user account and transmitting the user health rating to the user computing device.

In some embodiments, the disclosure describes a computer-implemented method comprising receiving a user identifier of a user associated with a user account from a user computing device. Based on the user identifier, the method may include extracting an account transaction history for the user account. The account transaction history may include one or more user transaction records each associated with a merchant. The method may include identifying a merchant category code for the merchant associated with each of the one or more user transaction records, each of the merchant category codes being one of a plurality of merchant category codes. The method may include assigning a merchant health rating to each merchant category code of the plurality of merchant category codes and determining a transaction health rating for each of the one or more user transaction records based at least partially on the merchant health rating for the identified merchant category code for each of the one or more user transaction records. Based at least partially on the transaction health rating of the one or more user transaction records, the method may include determining a user health rating associated with the user account and providing a graphical user interface to the user computing device that graphically depicts the user health rating associated with the user account over time.

Figure 1:
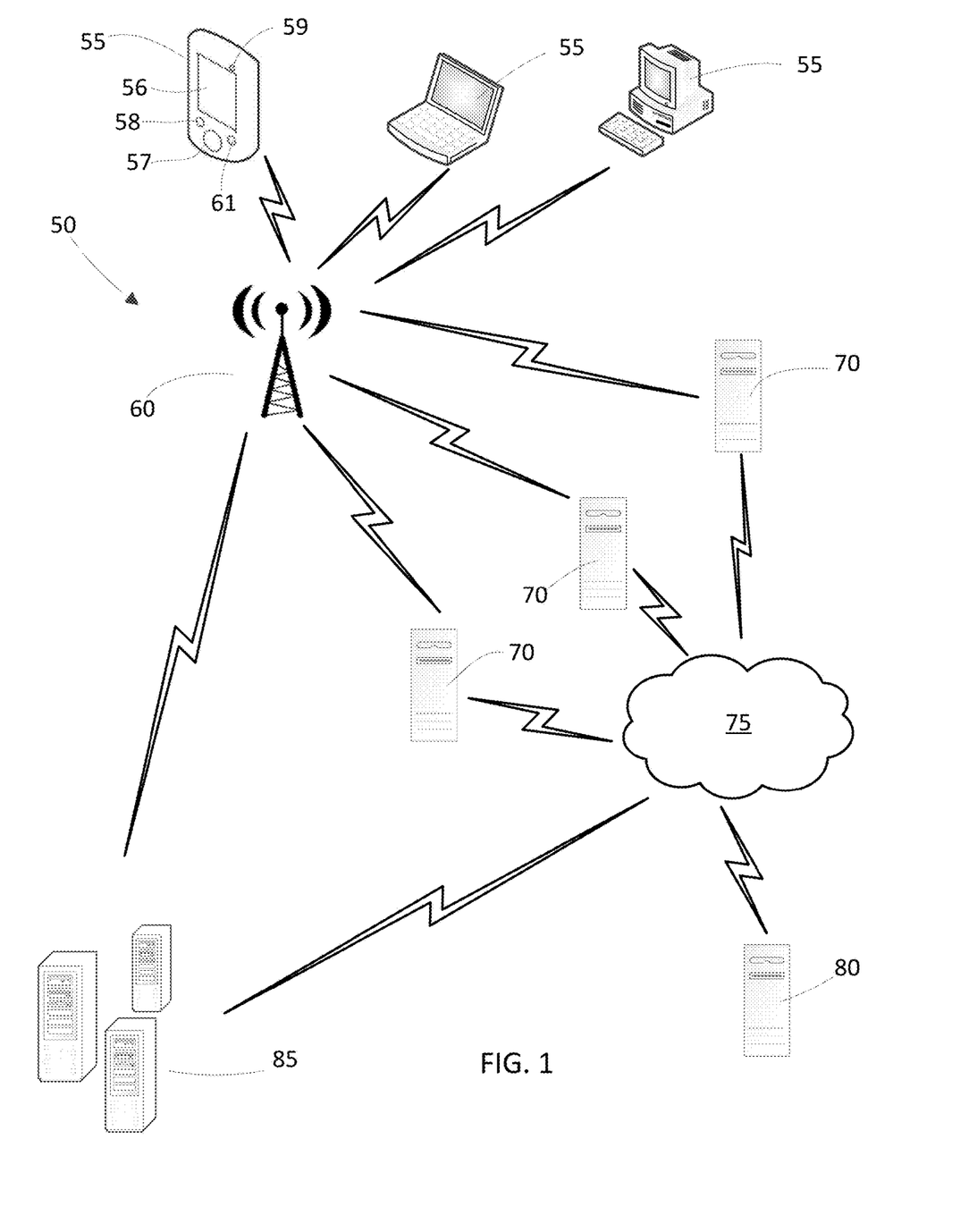
FIG. 1 is an illustration of the elements of an embodiment of a system that includes a health monitoring system as disclosed herein.

A high level illustration of some of the elements in a sample computing system 50 that may be physically configured to implement the health monitoring system and process is illustrated in FIG. 1. The system 50 may include any number of computing devices 55, such as smart phones or tablet computers, mobile computing devices, wearable mobile devices, desktop computers, laptop computers, or any other computing devices that allow users to interface with a digital communications network, such as digital communication network 60. Connection to the digital communication network 60 may be wired or wireless, and may be via the internet or via a cellular network or any other suitable connection service. Various other computer servers may also be connected via the digital communication network 60, such as one or more merchant servers 70, a payment server 80, and a health monitoring server 85. The payment server 80 may represent, for example, a credit card issuer, a bank, a payment processor, or another financial institution. Various of these servers or computer entities may also be connected through a secure payment network 75. The payment network 75 may be an electronic payment system used to accept, transmit, or process transactions made by users with payment cards for money, goods, or services, and to transfer information and funds among payment card issuers, merchants, payment card holders, payment processors, acquirers, etc. In the illustrated embodiment, at least one merchant server 70, the payment server 80, and the health monitoring server 85 may be connected via the payment network 75, but it is contemplated that other entities, such as acquirers, issuers, or token managers, may be connected as well. It is also contemplated that the health monitoring server 85 may also be connected to the one or more user devices 55 over the digital communication network 60.

In one embodiment, the computing device 55 may be a device that operates using a portable power source, such as a battery. The computing device 55 may also have a display 56 which may or may not be a touch sensitive display. More specifically, the display 56 may have a capacitance sensor, for example, that may be used to provide input data to the computing device 55. In other embodiments, an input pad 57 such as arrows, scroll wheels, keyboards, etc., may be used to provide inputs to the computing device 55. In addition, the computing device 55 may have a microphone 58 which may accept and store verbal data, a camera 59 to accept images and a speaker 61 to communicate sounds.

Figure 2:
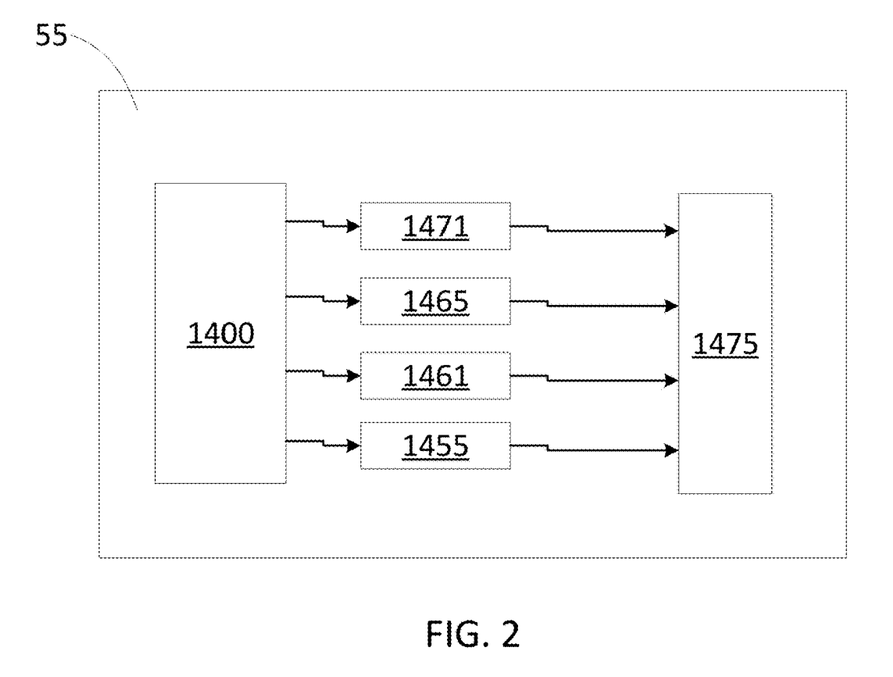
FIG. 2 is a schematic illustration of elements of an embodiment of an example computing device.
Figure 3:
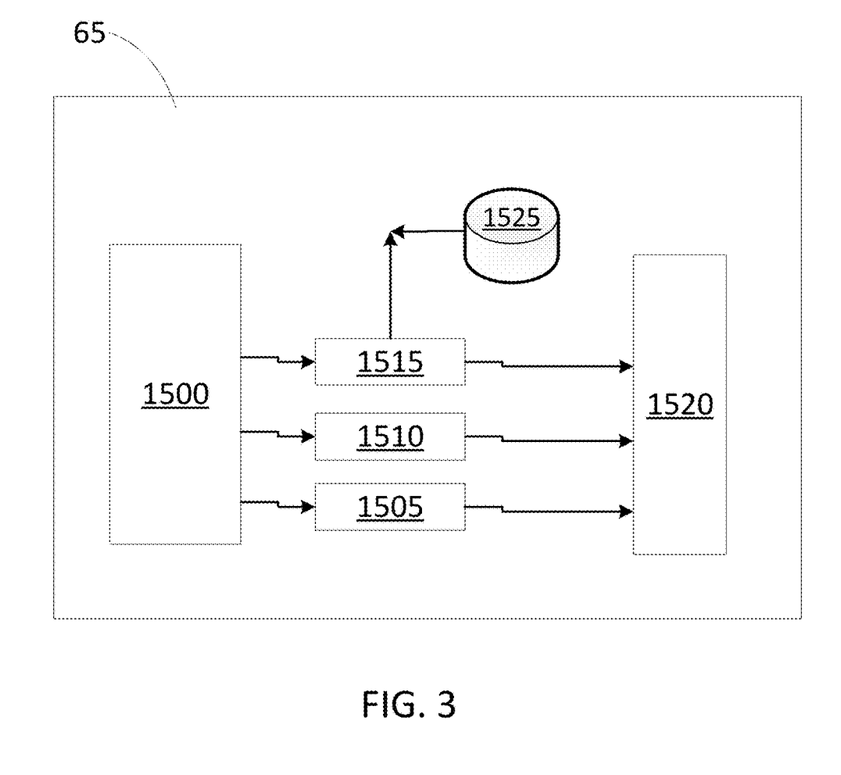
FIG. 3 is a schematic illustration of elements of an embodiment of a server type computing device.

FIG. 2 is a simplified illustration of the physical elements that make up an embodiment of a computing device 55 and FIG. 3 is a simplified illustration of the physical elements that make up an embodiment of a server type computing device, such as the health monitoring server 85, but the merchant servers 70 and the payment server 65, may reflect similar physical elements in some embodiments. Referring to FIG. 2, a sample computing device 55 is illustrated that is physically configured according to be part of the computing system 50 shown in FIG. 1. The portable computing device 55 may have a processor 1451 that is physically configured according to computer executable instructions. In some embodiments, the processor can be specially designed or configured to optimize communication between the server 85 and the computing device 55 relating to the health evaluation application described herein. The computing device 55 may have a portable power supply 1455 such as a battery, which may be rechargeable. It may also have a sound and video module 1461 which assists in displaying video and sound and may turn off when not in use to conserve power and battery life. The computing device 55 may also have volatile memory 1465 and non-volatile memory 1471. The computing device 55 may have GPS capabilities that may be a separate circuit or may be part of the processor 1451. There also may be an input/output bus 1475 that shuttles data to and from the various user input/output devices such as a microphone, a camera 59, a display 56, or other input/output devices. The portable computing device 55 also may control communicating with the networks, such as communication network 60 in FIG. 1, either through wireless or wired devices. Of course, this is just one embodiment of the portable computing device 55 and the number and types of portable computing devices 55 is limited only by the imagination.

The physical elements that make up an embodiment of a server, such as the health monitoring server 85, are further illustrated in FIG. 3. In some embodiments, the health monitoring server is specially configured to run the health monitoring system as described herein. At a high level, the health monitoring server 85 may include a digital storage such as a magnetic disk, an optical disk, flash storage, non-volatile storage, etc. Structured data may be stored in the digital storage such as in a database. More specifically, the server 85 may have a processor 1500 that is physically configured according to computer executable instructions. In some embodiments, the processor 1500 can be specially designed or configured to optimize communication between a portable computing device, such as computing device 55, and the server 85 relating to the health monitoring system as described herein. The server 85 may also have a sound and video module 1505 which assists in displaying video and sound and may turn off when not in use to conserve power and battery life. The server 85 may also have volatile memory 1510 and non-volatile memory 1515.

A database 1525 for digitally storing structured data may be stored in the memory 1510 or 1515 or may be separate. The database 1525 may also be part of a cloud of servers and may be stored in a distributed manner across a plurality of servers. There also may be an input/output bus 1520 that shuttles data to and from the various user input devices such as a microphone, a camera, a display monitor or screen, etc. The input/output bus 1520 also may control communicating with the networks, such as communication network 60 and payment network 75, either through wireless or wired devices. In some embodiments, a health monitoring controller for running the health evaluation application may be located on the computing device 55. However, in other embodiments, the health monitoring controller may be located on health monitoring server 85, or both the computing device 55 and the server 85. Of course, this is just one embodiment of the health monitoring server 85 and additional types of servers are contemplated herein.

In the embodiment illustrated in FIG. 1, the health monitoring server 85 may be connected to the merchant servers 70 either through the digital communication network 60, through the payment network 75 or through other connections. In some embodiments, the merchant servers 70 may be associated with any type of merchant offering goods or services for purchase with payment cards, whether those purchases are online or otherwise. For online purchases, the merchant server 70 or a group of servers may host a merchant website where the merchant's goods or services may be purchases by a user.

In some embodiments, the health monitoring system may be hosted on or otherwise run by the health monitoring server 85. In some embodiments, the health monitoring system may be hosted by another entity, such as an issuer using an issuer server or a merchant using a merchant server 70. In some embodiments, a user may access the health monitoring server 85 via a computing device 55 such as a smartphone, and may set up an account with the health monitoring system. The user may provide user information for one or more payment accounts provided by one or more card issuers or associated with one or more merchants. The health monitoring system may store the payment account information associated with the user into the user's account so that the system may monitor purchases and transactions made using each of the payment accounts.

The computing device 55 may be able to communicate with a computer server or a plurality servers, such as the health monitoring server 85, the one or more merchant servers 70, and the payment servers 80. The computing device 55 may be able to communicate in a variety of ways. In some embodiments, the communication may be wired such as through an Ethernet cable, a USB cable or RJ6 cable. In other embodiments, the communication may be wireless such as through Wi-Fi (802.11 standard), Bluetooth, cellular communication or near field communication devices. The communication may be direct to the server or may be through a digital communication network 60 such as cellular service, through the Internet, through a private network, through Bluetooth, etc.

In some embodiments, the health monitoring servers 85 may be associated with the health monitoring system, and may send and receive information to and from a user device 55 associated with the user payment accounts of a user. Specifically, software may be included on the user computing device 55 allowing notifications to be received from the health monitoring system via the digital communications network 60. In some embodiments, the software may be an application through which a user may complete transactions, such as banking, money transfer, merchant purchases, etc. In some embodiments, the software may be an add-on to a web browser included on the user computing device 55. In some embodiments, the health monitoring system's software may be an application installed on the user computing device 55 that allows for the use of other applications on the user computing device, such as applications provided by payment processor, issuer, bank, merchant, email service, payment provider, etc. In yet other embodiments, the health monitoring system may provide notifications using software native to the user computing device 55, such as SMS messaging or other notifications. In such embodiments, the health monitoring system may send notifications to the user device 55 regarding user health ratings and related information, such as are described in further detail below.

Figure 4:
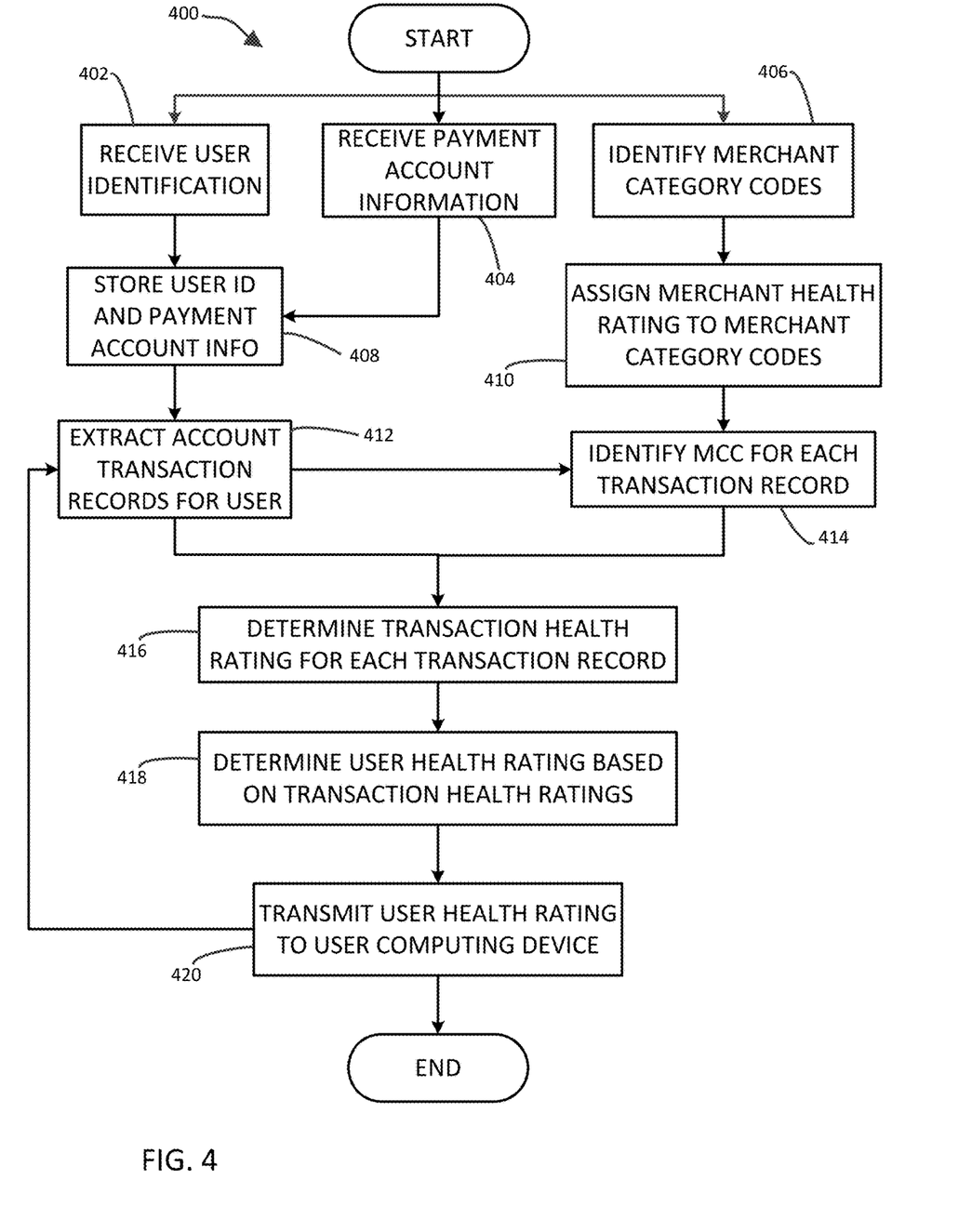
FIG. 4 is a flow chart of an embodiment of a method of using the health monitoring system described herein.

FIG. 4 is a flow chart of an embodiment 400 of a method of using the health monitoring system described herein. In some embodiments, the steps depicted in FIG. 4 may be performed by a health monitoring server, such as health monitoring server 85 in FIG. 1, or may be performed by a payment processor, an issuer, a bank, or any combination. In some embodiments, some of the steps shown may be performed on the health monitoring server, the user computing device, or a combination of both. At 402, the method may include receiving user identification information in order to set up a user account. For example, some embodiments may include receiving a user ID and password, demographic information such as age, sex, ethnic background, etc. At 404, the method may include receiving payment account information for one or more payment accounts associated with the user. At 408, in some embodiments, the payment account information may be stored along with the user identification information in a user account. In some embodiments, the payment accounts may be associated with payment servers such as payment server 80, and may be accessible via the payment network 75. In some embodiments, the user may provide account access to the one or more payment accounts to allow access to transaction history for the user accounts.

At 406, the method may include identifying a plurality of merchant category codes (MCC). In some embodiments, MCCs may be those defined by one or more retail financial services standards, such as ISO 18425. In some embodiments, MCCs may be used to classify businesses and the types of goods or services the business provides, and may be assigned by merchant type or by merchant name. MCCs may be assigned by a credit card company and may reflect a primary category in which the merchant does business. At 410, the method may include assigning a merchant health rating to each merchant category code based at least partially on the type of business and service the merchant category code represents. For example, MCCs indicating fast food service or alcohol sales may be assigned relatively negative or relatively low merchant health ratings. On the other hand, MCCs associated with health clubs, organic grocery stores, sports equipment, or other merchant types generally corresponding to healthier lifestyles may be assigned relatively positive or relatively high merchant health ratings. For example, in some embodiments, particular MCCs may be identified as indicating "positive" health outcomes (e.g., +1), "negative" health outcomes (e.g., -1), and "neutral" health outcomes (e.g., 0). In other embodiments, different MCCs may be assigned a numerical range of health outcomes, such as 0 through 10, 0 through 100, -10 through 10, or any other suitable rating system.

At 412, the method may include extracting account transaction history associated with the payment accounts included in the user account. For example, if information for a first payment account and a second payment account have been included in the user account, the method may retrieve account transaction history for each of the first and second payment accounts. In some embodiment, the transaction history may include one or more transaction records, each of which may be associated with a transaction with a merchant. At 414, the method may include identifying the MCC associated with each transaction record. In some embodiments, this may include identifying the MCC associated with the merchant for each transaction record. For example, if a transaction record includes a user transaction with a grocery store, that particular transaction record may be associated with the MCC for the grocery store merchant. In some embodiments, the account transaction history may be for a particular time period, such as weeks, months, years, etc. (e.g., one month, two months, six months, one year, five years, etc.).

At 416, the method may include determining a transaction health rating for each transaction record in the user's account transaction history, either overall or for a particular time period. In some embodiments, determining the transaction health rating for each transaction may include determining the merchant health rating associated with the MCC of the particular transaction record. For example, if the MCC for a particular transaction record indicates the merchant is a health foods store, the merchant health rating for that MCC may be positive, or score relatively high on a numerical health rating score, such as 8 out of 10. Accordingly, in some embodiments, the transaction health rating for that particular transaction record with the health foods store may also be positive, or 8 out of 10, for example. In contrast, for a transaction record in which the user has purchased something from merchant with an MCC associated with fast food restaurants, for example, the merchant health rating for that MCC (and thus that merchant) may be negative, or relatively low such as 3 out of 10. Accordingly, in such an example, the transaction health rating for that particular transaction record with the fast food restaurant merchant may be negative, or 3 out of 10. Those skilled in the art will understand that the provided ratings are merely examples and may be any of a variety of ratings.

In some embodiments, the transaction health ratings for the one or more transaction records may be determined using data or information alternative to or in addition to the merchant health rating associated with the MCC. In some embodiments, other behavior features of each transaction record may influence the transaction health rating for a particular transaction record, such as purchase time, frequency of purchases, consistency of purchases, etc. For example, the system may evaluate whether a particular transaction record includes a purchase from a fast food restaurant late at night. Such late-night purchases may be associated with negative health behavior. In some embodiments, the resulting transaction health rating may be even more negative (e.g., -2 instead of -1) than would have been indicated by the MCC alone, or may have a lower absolute score on a number scale (e.g., 2 out of 10 instead of 3 out of 10). In some embodiments, certain late night purchase (e.g., fast food) may be interpreted as a separate category of transaction that receives its own negative transaction health rating. Similarly, if transaction records show that a user is making frequent purchases (e.g., 3 or 4 times a week, etc.) from merchants associated with negative or relatively low merchant health ratings, the frequency of those purchases may result in additional negative ratings or reduced numerical ratings. In contrast, in some embodiments, frequently repeated or consistent transactions with merchants associated with positive or relatively high merchant health ratings may cause the system to award additional positive ratings or higher absolute transaction health ratings. For example, frequent transactions with a gym or health club may result in higher transaction health rating.

At 418, the method may include determining a user health rating for the user either for a particular time period or for all known times. The user health rating may be determined based in a variety of suitable ways while remaining within the spirit of the disclosure. In some embodiments, the user health rating may be determine at least partially based on the transactional health ratings. For example, the user health rating may be determined by summing up the transactional health ratings for each transaction record, or for the transaction records within a particular time period. In such embodiments, a positive grade transaction health rating may receive a +1, a negative grade transaction health rating may receive a -1, and a neutral transaction health rating may receive a 0. Table 1 below shows an exemplary set of transaction records along with associated transaction health ratings:

TABLE 1

| Transaction Record | Transaction Health Rating |
|---|---|
| Transaction #1 | −1 |
| Transaction #2 | 0 |
| Transaction #3 | +1 |
| Transaction #4 | +1 |
| Transaction #5 | +1 |
| TOTAL | +2 |

In the example in Table 1, the sum of each individual transaction health rating may be "+2", indicating a user health rating of +2 for a particular time period. Table 2 shows another example of summing transaction health ratings using a rating system with health ratings between 0 (worst health outcomes) and 10 (best health outcomes):

TABLE 2

| Transaction Record | Transaction Health Rating |
|---|---|
| Transaction #1 | 3 |
| Transaction #2 | 4 |
| Transaction #3 | 8 |
| Transaction #4 | 1 |
| Transaction #5 | 9 |
| TOTAL | 25 |

In the example in Table 2, the sum of each individual transaction health rating may be 25. Of course, those skilled in the art will recognize that Tables 1 and 2 represent merely exemplary transaction records and corresponding scores, and that the records and scores in any given embodiment will be infinitely variable.

In some embodiments, the system may evaluate additional behavioral data to determine the user health rating. As described above, time of purchases, frequency of transactions with particularly merchants with MCC, or consistency of purchases may influence the user health rating. For example, consistent healthy purchases with a particular merchant may increase the user health rating to be greater than the sum of the transaction health ratings. In some embodiments, exceeding a first threshold number of transactions with a particular merchant or merchants associated with an MCC having a positive merchant health rating may increase the user health rating by first rating increase (e.g., 1 point), while exceeding a second threshold number of transactions with a particular merchant or merchants associated with an MCC having a positive merchant health rating may increase the user health rating by second rating increase greater than the first rating increase (e.g., 2 points). In contrast, in some embodiments, exceeding a first threshold number of transactions with a particular merchant or merchants associated with an MCC having a negative merchant health rating may decrease the user health rating by first rating decrease (e.g., −1 point), while exceeding a second threshold number of transactions with a particular merchant or merchants associated with an MCC having a negative merchant health rating may decrease the user health rating by second rating decrease greater than the first rating decrease (e.g., −2 points). Those skilled in the art may understand that other user purchase behaviors may also influence the user health rating.

In some embodiments, the user health rating may be determined using artificial intelligence (AI) and/or machine learning techniques. For example, in some embodiments, a plurality of example transaction histories with a plurality of transaction records may be evaluated manually to indicate the types of transactions, purchases, merchant encounters, and other behavior habits that may indicate a positive or negative user health rating. The example transaction histories may then be used to train a classification algorithm that may take what it learns from the example transaction histories and apply it to new transaction histories to determine whether they reflect healthy or unhealthy purchase and/or behavioral habits. Those skilled in the art will understand that various different classification algorithms may be used, such as logistic regression, random forest, Naïve Bayes classifier, etc.

In some embodiments, the user health rating may be influenced by the particular demographic traits of the individual user. For example, a user's transaction health rating may be influenced by generally known health considerations related to a user's age, sex, ethnicity, etc. In some embodiments, the negative effect of particular unhealthy purchases, such as fast food or alcohol, may be increased for users as user age increases. For example, if a 25 year old male user and a 65 male user each purchase alcohol or fast food three times a week, the user health rating for the 25 year old male may be effected by a relatively small amount, while the user health rating for the 65 year old male may be effected by a relatively large amount. Those skilled in the art will recognize that various other health factors may be intuited based on user age and other demographic factors. In some embodiments, the system may determine user age based on the user profile, while in some embodiments, the system may determine user age through a segmentation platform API.

At 420, the method may include transmitting the user health rating to a computer device associated with the user, such as user computing device 55 of FIG. 1. The user computing device may receive the user health rating in any of a variety of ways, including text message, multimedia message, e-mail, notifications, etc. In some embodiments, the user computing device may run a health evaluation application with which the user may interface with the health monitoring system. In some embodiments, the user may request a current user health rating, or a user health rating based on a particular time period, or for historical user health ratings over past time periods (e.g., weeks, months, years, etc.). In some embodiments, the health evaluation application may provide access to graphical representations of the user health rating, the user health rating over time, graphical representations of the particular types of transactions that are directing the user health rating positively or negatively, and may provide advice or suggestions as to how a user may improve the user health rating over time. Graphical representations of user data related to the user health rating are described in greater detail below.

Figure 5:
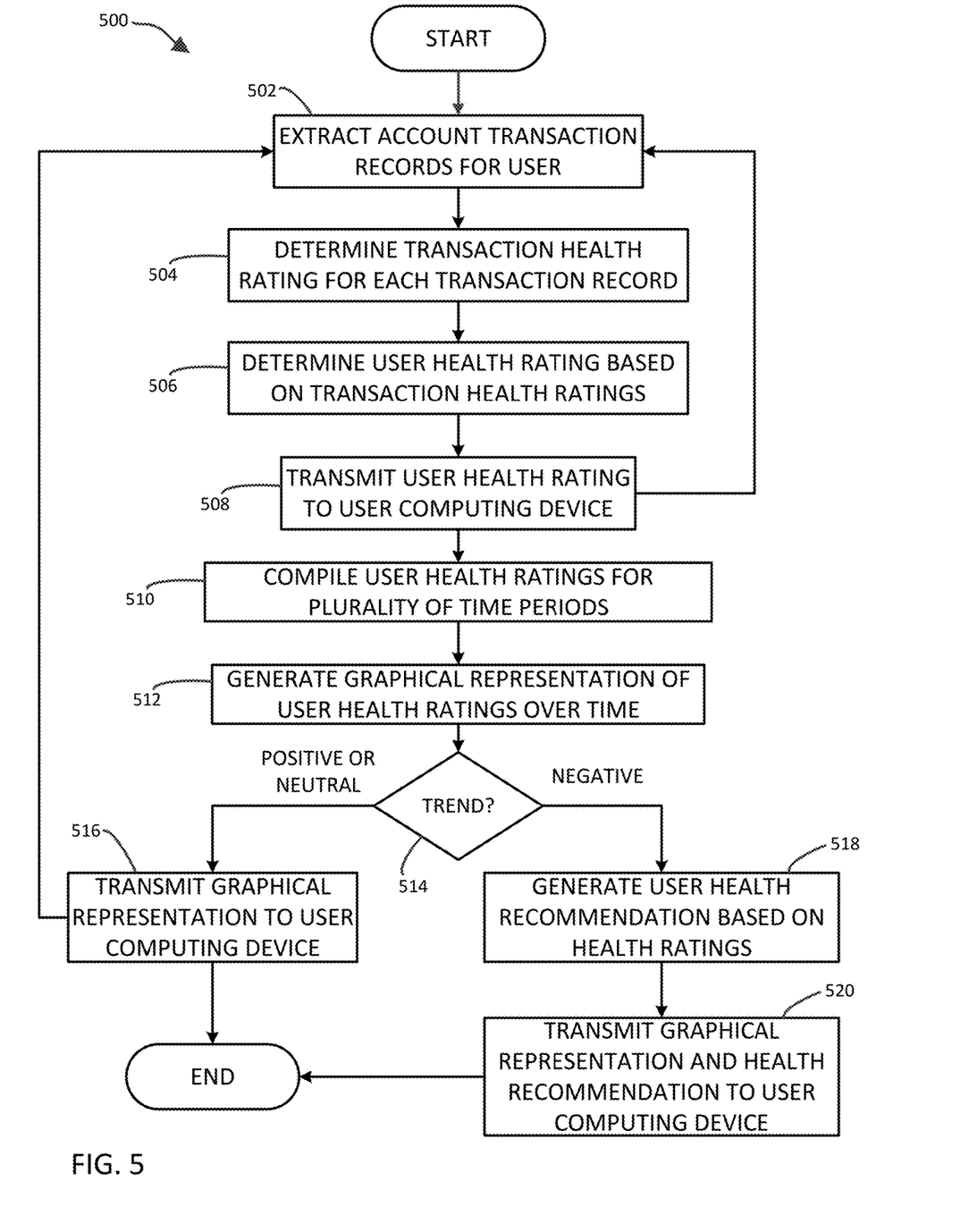
FIG. 5 is a flow chart of another embodiment of a method of using the health monitoring system described herein.

FIG. 5 is a flow chart of another embodiment 500 of the health monitoring system. At 502, the method may include extracting account transaction history for the user, where the transaction history may include one or more transaction records for a particularly time period. At 504, the method may include determining a transaction health rating for each transaction record in the transaction history and, at 506, determining a user health rating based on the one or more transaction health ratings. The method may also include transmitting the user health rating to the user computing device, sometimes in response to a request by the user via the health monitoring application. Steps 502-508 may be similar to steps 412, 416, 418, and 420 described above in reference to FIG. 4, where they are described in more detail.

At 510, the method may include compiling a plurality of user health ratings for a respective plurality of time periods.

For example, the health monitoring system may determine user health ratings based on user behavior and transactions each month, each week, each quarter, or for any other suitable time interval. At 512, the method may include generating a graphical representation of the compiled user health ratings over time. In some embodiments, the graphical representation may be any of a variety of forms, including bar graphs, line graphs, scatter plots, pie charts, etc. Example graphical representations are described below with reference to FIG. 6. In some embodiments, the graphical representations may be generated at the health monitoring server and transmitted to the user computing device, while in some embodiments, the graphical representations may generated at the user computing device based on information received from the health monitoring server.

In some embodiments, at 514, the method may include evaluating trends in the user health ratings over some interval or intervals of time to determine whether, for example, the user health rating is improving or worsening over time (e.g., is there a positive or negative trend in the user health rating). In some embodiments, if the system determines that the user health rating has a positive trend over time (e.g., is improving month-to-month) or neutral trend over time (e.g., neither increasing or decreasing), the method at 516, may include transmitting the generated graphical representation to the user computing device. In some embodiments, if the system determines that the user health rating has a negative trend over time (e.g., is worsening month-to-month), the method may include, at 518, generating a user health recommendation based on the user health ratings and, at 520, transmitting the graphical representation and the health recommendation to the user computing device. The user health recommendation may be based at least partially on the categorization of the transaction records in the user's account transaction history. For example, the system may analyze the user's transaction records and determine that a relatively large portion of the user's negative or relatively low transaction health ratings are from a particular merchant or a particular type of merchant (e.g., fast food restaurants). The system may generate a recommendation that the user reduce the number of transactions taking place with that particular merchant or type of merchant in order to increase the user health rating. Similarly, the system may determine that the account transaction history includes a relatively low number of transactions with merchants or types of merchants that are associate with positive or relatively high transaction health ratings (e.g., health clubs). In such embodiments, the system may generate a recommendation that the user increase the number of transactions with that particular type of merchant in order to increase the user health rating.

In some embodiments, the health recommendation may be provided without providing a graphical representation, but may be illustrated using the graphical representation as well. In some embodiments, the system may generate a projected user health rating and corresponding graphical representation based on the health recommendation to show the user where their user health rating would be if they were to continue with similar purchasing behavior except following the health recommendation for one or more types of purchases or merchants. It should be understood by those skilled in the art that the graphical representations of the user health rating and the health recommendations may occur on the health monitoring server or the user computing device, or both in some embodiments. In some embodiments, the user may use the health evaluation application to request a health recommendation from the system based on the user's transaction history, and the health recommendation may be provided automatically in some embodiments.

Figure 6:
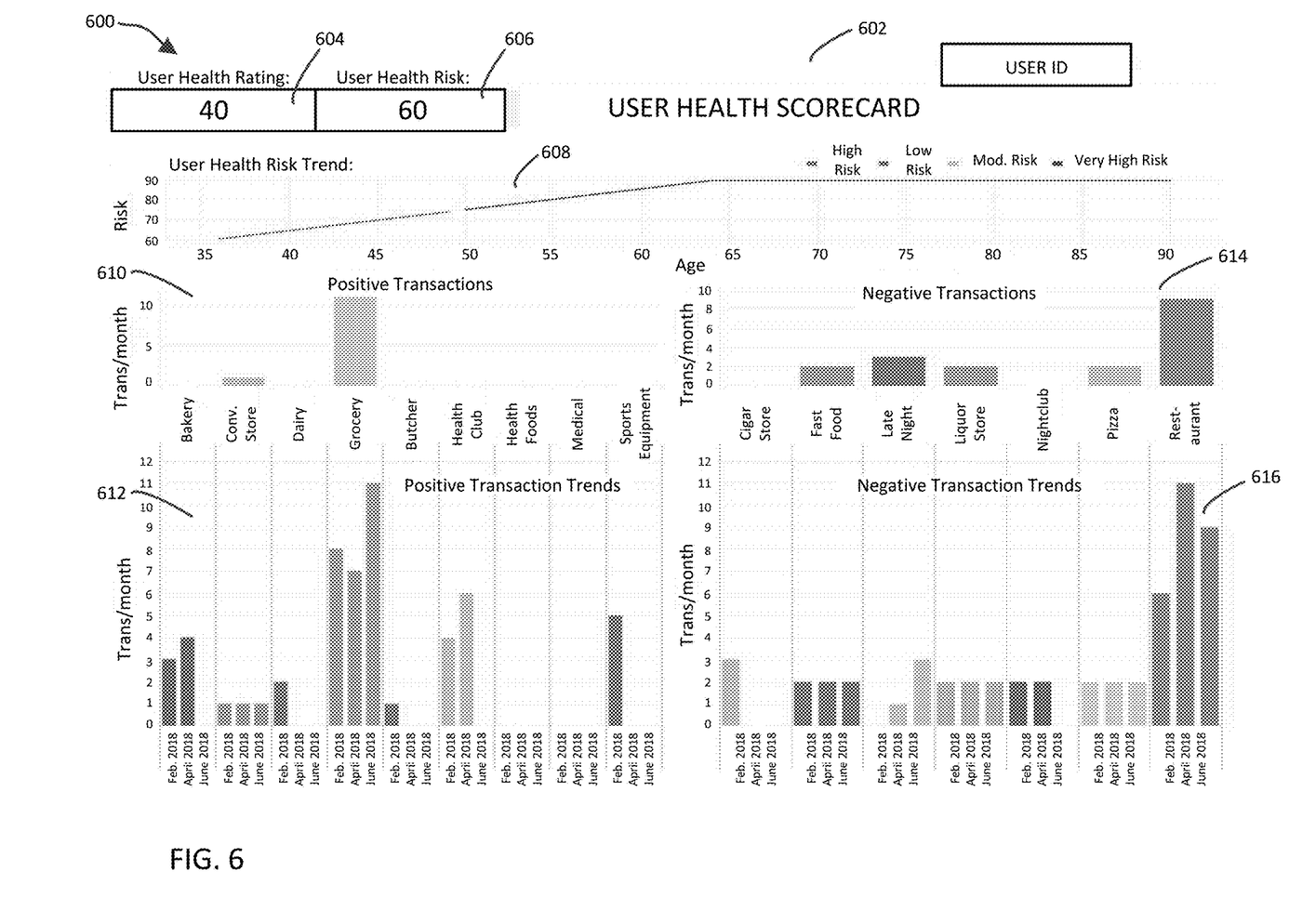
FIG. 6 is an embodiment of an exemplary graphical user interface of the health monitoring system described herein.

FIG. 6 show an example screenshot from and embodiment of a graphical user interface (GUI) 600 that may be provided in the health monitoring system via the health evaluation application. It should be understood that the health evaluation application described herein may provide many additional GUIs consistent with the disclosure, and that the GUI 600 shown in FIG. 6 is merely exemplary. In some embodiments of the health evaluation application, the GUI 600 may include a user health scorecard 602. The user health scorecard 602 may include various visual and/or graphical representations of information related to the user health rating. For example, the user health scorecard 602 may show a user health rating 604 and a user health risk 606. In some embodiments, the user health rating may be based on a scale between 0 and 100, and a user health risk may be the compliment of the user health rating on the 100 point scale (e.g., user health risk=100—user health rating). However, it should be understood that the user health rating and a user health risk may be determined in many suitable ways consistent with the disclosure. The user health scorecard 602 may also include a graphical representation of a user health risk trend 608. In such embodiments, the user health risk may be plotted on a graph's vertical axis and the age of the user may be plotted along the graph's horizontal axis. In some embodiments, the user health risk trend 608 may depict the actual user health risk for the ages of a user that have already past, and the projected user health risk for later ages. In the exemplary user health risk trend plot 608 in FIG. 6, the user's health risk is plotted when the user is about 35 years old, and the trend is illustrated from ages 35 to 90. In some embodiments, the user health risk trend line may be in multiple colors or have other visual variations that may indicate varying levels of risk, e.g., high risk, low risk, moderate risk, or very high risk. In some embodiments, the user health scorecard 602 may include a graphical depiction of the user health rating 604 over time instead of or in addition to the user health risk 606.

The user health scorecard 602 may also include graphical representations of a user's purchasing patterns during a particular time interval or as an average rate. For example, the user health scorecard 602 may include a bar graph of positive transactions 610 (e.g., transactions made with merchants associated with positive health outcomes or with an MCC associated with positive health outcomes). The positive transactions graph 610 may plot number of transactions per month on a vertical axis and the classification of merchant on the horizontal axis. In some embodiments, the positive transactions graph 610 may depict transaction data from a particular time period, or may depict an average number of transactions over a time interval, such as per month. For example, the positive transaction graph 610 in FIG. 6 includes the transactions in the previous month made with several exemplary positive health merchants, such as bakeries, convenient stores, dairy products, grocery stores, butcher, health club, health food store, medical, and sports equipment. The user health scorecard 602 may additionally include a positive transaction trends graph 612 that may reflect the number of transactions in the previous several time intervals, e.g., the previous three months. The positive transaction trends graph 612 in FIG. 6 shows transactions per month on the vertical axis, and three separate months per merchant category on the horizontal axis, using the same merchant categories as in the positive transactions graph

610. By illustrating a graphical representation of a set of previous time intervals, a user may more easily see trends in purchases over time.

In some embodiments, the user health scorecard 602 may include a bar graph of negative transactions 614 (e.g., transactions made with merchants associated with negative health outcomes or with an MCC associated with negative health outcomes). The negative transactions graph 614 may plot number of transactions per month on a vertical axis and the classification of merchant on the horizontal axis. In some embodiments, the negative transactions graph 614 may depict transaction data from a particular time period, or may depict an average number of transactions over a time interval, such as per month. For example, the negative transaction graph 614 in FIG. 6 includes the transactions in the previous month made with several exemplary negative health merchants, such as cigar stores, fast food restaurants, late food purchases, liquor stores, nightclubs, pizza, and restaurants. The user health scorecard 602 may additionally include a negative transaction trends graph 616 that may reflect the number of transactions in the previous several time intervals, e.g., the previous three months. The negative transaction trends graph 616 in FIG. 6 shows transactions per month on the vertical axis, and three separate months per merchant category on the horizontal axis, using the same merchant categories as in the negative transactions graph 614. By illustrating a graphical representation of a set of previous time intervals, a user may more easily see trends in purchases over time.

By implementing the teachings of the disclosure, users may more readily understand the health ramifications of their purchasing habits and, as a result, make changes to improve their health outcomes over time. The health monitoring system described herein solve the technical problem of compiling user transaction data in a way that may be beneficial to a user's health with a technical solution of determining a user health rating based on a user's transaction history. Thus, the health monitoring system described herein has a practical application of improving user health outcomes, which may increase user's quality of life, decrease overall medical costs, and potentially prolong user life expectancy.

The various participants and elements described herein may operate one or more computer apparatuses to facilitate the functions described herein. Any of the elements in the above-described Figures, including any servers, user terminals, or databases, may use any suitable number of subsystems to facilitate the functions described herein.

Any of the software components or functions described in this application, may be implemented as software code or computer readable instructions that may be executed by at least one processor using any suitable computer language such as, for example, Java, C++ or Perl using, for example, conventional or object-oriented techniques. In some examples, the at least one processor may be specifically programmed.

The software code may be stored as a series of instructions, or commands on a non-transitory computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

It may be understood that the present disclosure as described above can be implemented in the form of control logic using computer software in a modular or integrated manner. Based on the disclosure and teachings provided herein, a person of ordinary skill in the art may know and appreciate other ways and/or methods to implement the present disclosure using hardware and a combination of hardware and software.

The above description is illustrative and is not restrictive. Many variations of the disclosure will become apparent to those skilled in the art upon review of the disclosure. The scope of the disclosure should, therefore, be determined not with reference to the above description, but instead should be determined with reference to the pending claims along with their full scope or equivalents.

One or more features from any embodiment may be combined with one or more features of any other embodiment without departing from the scope of the disclosure. A recitation of "a", "an" or "the" is intended to mean "one or more" unless specifically indicated to the contrary.

One or more of the elements of the present system may be claimed as means for accomplishing a particular function. Where such means-plus-function elements are used to describe certain elements of a claimed system it will be understood by those of ordinary skill in the art having the present specification, figures and claims before them, that the corresponding structure is a general purpose computer, processor, or microprocessor (as the case may be) programmed (or physically configured) to perform the particularly recited function using functionality found in any general purpose computer without special programming and/or by implementing one or more algorithms to achieve the recited functionality. As would be understood by those of ordinary skill in the art that algorithm may be expressed within this disclosure as a mathematical formula, a flow chart, a narrative, and/or in any other manner that provides sufficient structure for those of ordinary skill in the art to implement the recited process and its equivalents.

While the present disclosure may be embodied in many different forms, the drawings and discussion are presented with the understanding that the present disclosure is an exemplification of the disclosed principles and is not intended to be limited to the embodiments illustrated.

The present disclosure provides a solution to the long-felt need described above. In particular, the system and the methods described herein may be configured to efficiently provide an evaluation of user health based on user behaviors in real time, or as monitored and evaluated over time. Further advantages and modifications of the above described system and method will readily occur to those skilled in the art. The disclosure, in its broader aspects, is therefore not limited to the specific details, representative system and methods, and illustrative examples shown and described above. Various modifications and variations can be made to the above specification without departing from the scope or spirit of the present disclosure, and it is intended that the present disclosure covers all such modifications and variations provided they come within the scope of the following claims and their equivalents.

The invention claimed is:

1. A computer-implemented method comprising:
    identifying a plurality of merchant category codes;
    assigning a merchant health rating to each of the plurality of merchant category codes;
    receiving, via a digital communication network, a user identifier of a user associated with a user account from a user computing device;
    based on the user identifier, extracting an account transaction history for the user account, the account transaction history including one or more user transaction records each associated with a merchant;

identifying a merchant category code of the plurality of merchant category codes for the merchant associated with each of the one or more user transaction records;

determining a transaction health rating for each of the one or more user transaction records based at least partially on the merchant health rating for the identified merchant category code for each of the one or more user transaction records;

based at least partially on the transaction health rating of the one or more user transaction records, determining a user health rating associated with the user account;

compiling a plurality of user health ratings over a plurality of time periods and generating a graphical representation of the plurality of user health ratings over the plurality of time periods;

generating at least one user health recommendation based on one or more of the transaction health ratings for each of the one or more user transaction records; and transmitting, via the digital communication network, the graphical representation to the user computing device, the user computing device being configured to display the graphical representation of user health ratings via a graphical user interface (GUI), wherein the method is performed using one or more processors.

2. The method of claim 1, wherein the account transaction history includes a transaction time for each respective user transaction record, and wherein determining the transaction health rating is based at least partially on the transaction time of each respective user transaction record.

3. The method of claim 1, wherein the account transaction history pertains to a predetermined time period.

4. The method of claim 1 further comprising providing, via the GUI, a projected user health rating based on the at least one user health recommendation.

5. The method of claim 1, wherein the merchant health rating is one of a positive grade, a negative grade, or a neutral grade.

6. The method of claim 1, wherein the transaction health rating is one of a positive grade, a negative grade, or a neutral grade.

7. The method of claim 1, wherein the merchant health rating is a number.

8. The method of claim 1, wherein the at least one user health recommendation includes a recommendation that the user reduce a number of transactions with merchants having a merchant health rating below a predetermined health rating threshold.

9. The method of claim 1, wherein the user health rating is at least partially based on an age of the user.

10. A computer-implemented method comprising:
receiving, via a digital communication network, a user identifier of a user associated with a user account from a user computing device;

based on the user identifier, extracting an account transaction history for the user account, the account transaction history including a plurality of user transaction records each associated with a merchant, the plurality of user transaction records including a first user transaction record associated with a first merchant and a second user transaction record associated with a second merchant;

identifying a first merchant category code for the first merchant and a second merchant category code for the second merchant, wherein the first merchant category code is associated with a first merchant health rating and the second merchant category code is associated with a second merchant health rating;

determining a first transaction health rating for the first user transaction record based at least partially on the first merchant health rating and a second transaction health rating for the second user transaction record based at least partially on the second merchant health rating;

based at least partially on the first transaction health rating and the second transaction health rating, determining a first user health rating for a first time period associated with the user account;

generating a graphical representation of a plurality of user health ratings for a plurality of time periods including the first user health rating in the first time period;

generating at least one user health recommendation based on one or more of the plurality of user health ratings; and transmitting, via the digital communication network, the graphical representation to the user computing device, the user computing device being configured to display the graphical representation of user health ratings via a graphical user interface (GUI), wherein the method is performed using one or more processors.

11. The method of claim 10, wherein the account transaction history includes a transaction time for each user transaction record, and wherein determining the first transaction health rating is based at least partially on the transaction time of the first user transaction record and the second transaction health rating is based at least partially on the transaction time of the second user transaction record.

12. The method of claim 10, wherein the account transaction history pertains to a predetermined time period.

13. The method of claim 10 further comprising providing, via the GUI, a projected user health rating based on the at least one user health recommendation.

14. The method of claim 10, wherein the first and second merchant health ratings are each one of a positive grade, a negative grade, or a neutral grade.

15. The method of claim 10, wherein the first and second transaction health ratings are each one of a positive grade, a negative grade, or a neutral grade.

16. The method of claim 10, wherein each of the first and second merchant health ratings are a number.

17. The method of claim 10, wherein the at least one user health recommendation includes a recommendation that the user reduce a number of transactions with merchants having a merchant health rating below a predetermined health rating threshold.

18. The method of claim 10, wherein the user health rating is at least partially based on an age of the user.

19. A computer-implemented method comprising:
receiving, via a digital communication network, a user identifier of a user associated with a user account from a user computing device;

based on the user identifier, extracting an account transaction history for the user account, the account transaction history including one or more user transaction records each associated with a merchant;

identifying a merchant category code for the merchant associated with each of the one or more user transaction records, each of the merchant category codes being one of a plurality of merchant category codes;

assigning a merchant health rating to each merchant category code of the plurality of merchant category codes;

determining a transaction health rating for each of the one or more user transaction records based at least partially on the merchant health rating for the identified merchant category code for each of the one or more user transaction records;

based at least partially on the transaction health rating of the one or more user transaction records, determining a user health rating associated with the user account;

generating a graphical representation of a plurality of user health ratings over a plurality of time periods;

generating at least one user health recommendation based on one or more of the transaction health ratings for each of the one or more user transaction records; and providing, via the digital communication network, a graphical user interface to the user computing device that graphically depicts the graphical representation of the plurality of user health ratings, wherein the method is performed using one or more processors.

20. The method of claim 19, wherein the user health rating is at least partially based on an age of the user.

* * * * *